US00PP14795P2

(12) United States Plant Patent
Danziger

(10) Patent No.: US PP14,795 P2
(45) Date of Patent: May 18, 2004

(54) GYPSOPHILA NAMED 'DANGYPINK'

(50) Latin Name: *Gypsophila paniculata*
Varietal Denomination: Dangypink

(75) Inventor: Gabriel Danziger, Nir-Zvi (IL)

(73) Assignee: Danziger "Dan" Flower Farm, Hashiva (IL)

( * ) Notice: Subject to any disclaimer, the term of this patent is extended or adjusted under 35 U.S.C. 154(b) by 0 days.

(21) Appl. No.: 10/339,346

(22) Filed: Jan. 10, 2003

(51) Int. Cl.[7] ..... A01H 5/00
(52) U.S. Cl. ..... Plt./354
(58) Field of Search ..... Plt./354

*Primary Examiner*—Kent Bell
(74) *Attorney, Agent, or Firm*—Foley & Lardner

(57) ABSTRACT

A new and distinct Gypsophila plant named 'Dangypink' characterized by having a pinkish white semi-double flower, globular shape, 7–9 mm corolla diameter, wide spread inflorescence; 90–120 cm plant height, semi erect, branching along main stem; suitable as a commercial product for cut flowers; and vigorous growth habit.

2 Drawing Sheets

Latin name of the genus and species of the plant claimed: *Gypsophila paniculata.*
Variety denomination: Dangypink.

BACKGROUND OF THE INVENTION

The present invention relates to a new and distinct cultivar of Gypsophila plant, botanically known as *Gypsophila paniculata*, hereinafter referred to by the cultivar name 'Dangypink'.

The new cultivar originated from a cross made in a controlled breeding program in Mishmar Hashiva Israel. The female parent is a *Gysophila paniculata* proprietary, unpatented cultivar designated '96-184'. The male parent is a *Gypsophila paniculata* proprietary, unpatented cultivar designated 'P2000'. 'Dangypink' was discovered and selected by the inventor, Gabriel Danziger, as a flowering plant within the progeny of the stated cross in a controlled environment in Mishmar Hashiva, Israel.

Asexual reproduction of the new cultivar by removing a cutting from the initial plant was first performed in December, 2000 in Mishmar Hashiva, Israel and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'Dangypink' which in combination distinguish this Gypsophila as a new and distinct cultivar:

1. Pinkish white semi-double flower, globular shape, 7–9 mm corolla diameter;
2 Wide spread inflorescence;
3. 90–120 cm plant height, semi-erect, branching along main stem;
4. Suitable as a commercial product for cut flowers; and
5. Vigorous growth habit.

'Dangypink' has not been observed under all possible environmental conditions. The phenotype of the new cultivar may vary significantly with variations in environment such as temperature, light intensity, and daylength without any change in the genotype of the plant. The following observations, measurements and values describe the new cultivar as grown in Mishmar Hashiva, Israel under conditions which closely approximate those generally used in commercial practice.

Of the many commercial cultivars known to the present inventor, the most similar in comparison to 'Dangypink' is the Gypsophila cultivar 'Flamingo' (unpatented). In comparison to Flamingo, 'Dangypink' has a bigger flower and has a more vigorous growth habit.

The following is a comparison chart between 'Dangypink' and the parental cultivars.

TABLE 1

| Characteristic | 'Dangypink' | Female parent '96–184' | Male parent 'P2000' |
|---|---|---|---|
| Flower | Semi-double, 7–9 mm diameter, pinkish-white in color | Double, 9–11 mm diameter, white in color | Double, 9–11 mm diameter, pink in color |
| Inflorescence | Wide spread | Conical | Wide spread |
| Growth Habit | Semi-erect, branching along the main stem | Erect, branching from the plant base | Semi-erect, branching along the main stem |

BRIEF DESCRIPTION OF THE DRAWING

The accompanying photographic drawings show typical flowers and foliage of a 12 week old 'Dangypink' plant, with colors being as true as possible with illustrations of this type. The first drawing is a view of a flowering stem of 'Dangypink'. The second drawing is a a close-up view of the flowers and buds of 'Dangypink'.

DETAILED BOTANICAL DESCRIPTION

The following observations, measurements and values describe the new cultivar at 12 weeks, as grown in Mishmar Hashiva, Israel under conditions which closely approximate those generally used in commercial practice. Regular cultural practices common for Gypsophila in commercial fields were applied. Avoid excess GA or lighting; lighting unnecessary under long day conditions of 12 hours and more. Color references are made to The Royal Horticultural Society Colour Chart (R.H.S.), except where general colors of ordinary significance are used. Color values were taken under daylight conditions at approximately noon in Mishmar Hashiva Israel.

Propagation: Stem cutting.

Plant:

*General appearance and form.*—Height: 90–120 cm. Width: 60–80 cm. Habit: Apical dominance, branching along main stem. Growth habit: Vigorous; from planting to a fully grown flowering bush, 90–120 cm growth in 12 weeks in summer. Form: Semi upright bush type. Flowering response: Long day. Flowering season: Summer, all year with suplement lighting. Winter hardiness: Temperature tolerant down to 0° C. Lastingness of the individual bloom: As a cut flower 6–8 days at room temperature; 4–5 days on the plant. Lastingness of the inflorescence: As a cut flower 10–12 days at room temperature; 8–10 days on the plant. Fragrance: Typical of gypsophila.

Foliage:

*Amount.*—Little.

*Attachment.*—Sessile.

*Overall shape of leaf.*—Lanceolate. Base: Truncate. Tip: Acuminate.

*Margin.*—Entire.

*Texture.*—Rough.

*Main color of upper surface.*—Mature leaf: Green 137-A. Immature leaf: Green 137-A.

*Main color of lower surface.*—Mature leaf: Green 137-B. Immature leaf: Green 137-B.

*Venation.*—None.

*Size.*—Length: 6–7 cm. Width: 1–1.5 cm.

*Stipules.*—None.

Inflorescence:

*Natural flowering season.*—Summer, long day.

*Corolla.*—Form: Semi double. Shape: Globular. Average number: 1000–1200 flowers per flowering stem. Diameter: 7–9 mm. Petal number: 30–35. Petal shape: Spatulate with emarginated tip; margin: entire. Petal size: 3 mm length; 1 mm width. Petal markings: Transparent margin. Petal color: Pinkish white RHS 56-C, both surfaces (color intensity dependent on climactic conditions). Sepal shape: Lanceolate; acuminate apex; margin: entire. Sepal size: 3 mm length; 1 mm width. Sepal color: Green, RHS 141C.

*Stem.*—Habit: Upright, long and stable. Average length: 80–100 cm. Average diameter: 4–5 mm. Color: Yellow-Green RHS 144-A. Internode length: 6–8 cm.

*Spur.*—None.

*Bud.*—Response: Long day. Color: Pinkish white. Size before opening: Length 4 mm, width 3 mm. Shape: Oblate. Pedicel length: 9–11 mm. Pedicel color: Yellow-Green 146-A.

Reproductive organs:

*Stamen.*—5–10 in number, however seldom seen, white in color.

*Seeds.*—Width: 1 mm. Length: 1 mm. Shape: Kidney shaped. Color: Black-Brown.

*Fruit.*—Light Brown.

*Anthers.*—5–10, seldom seen, white in color.

*Pollen.*—White.

*Stigma.*—2 pistils convex, white in color.

*Ovary.*—Green.

Disease resistance: No susceptibility to disease was observed under regular growing conditions.

I claim:

1. A new and distinct Gypsophila plant named 'Dangypink', substantially as illustrated and described herein.

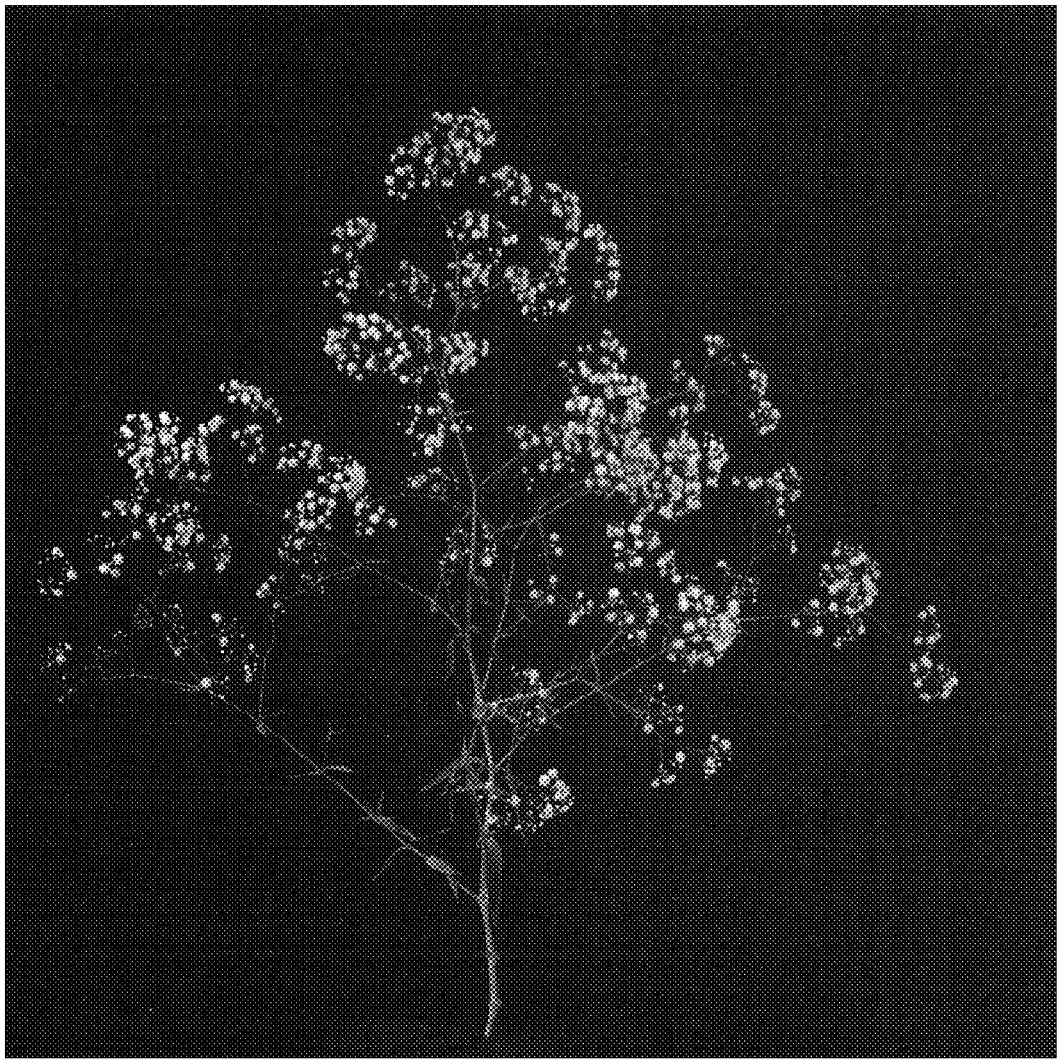

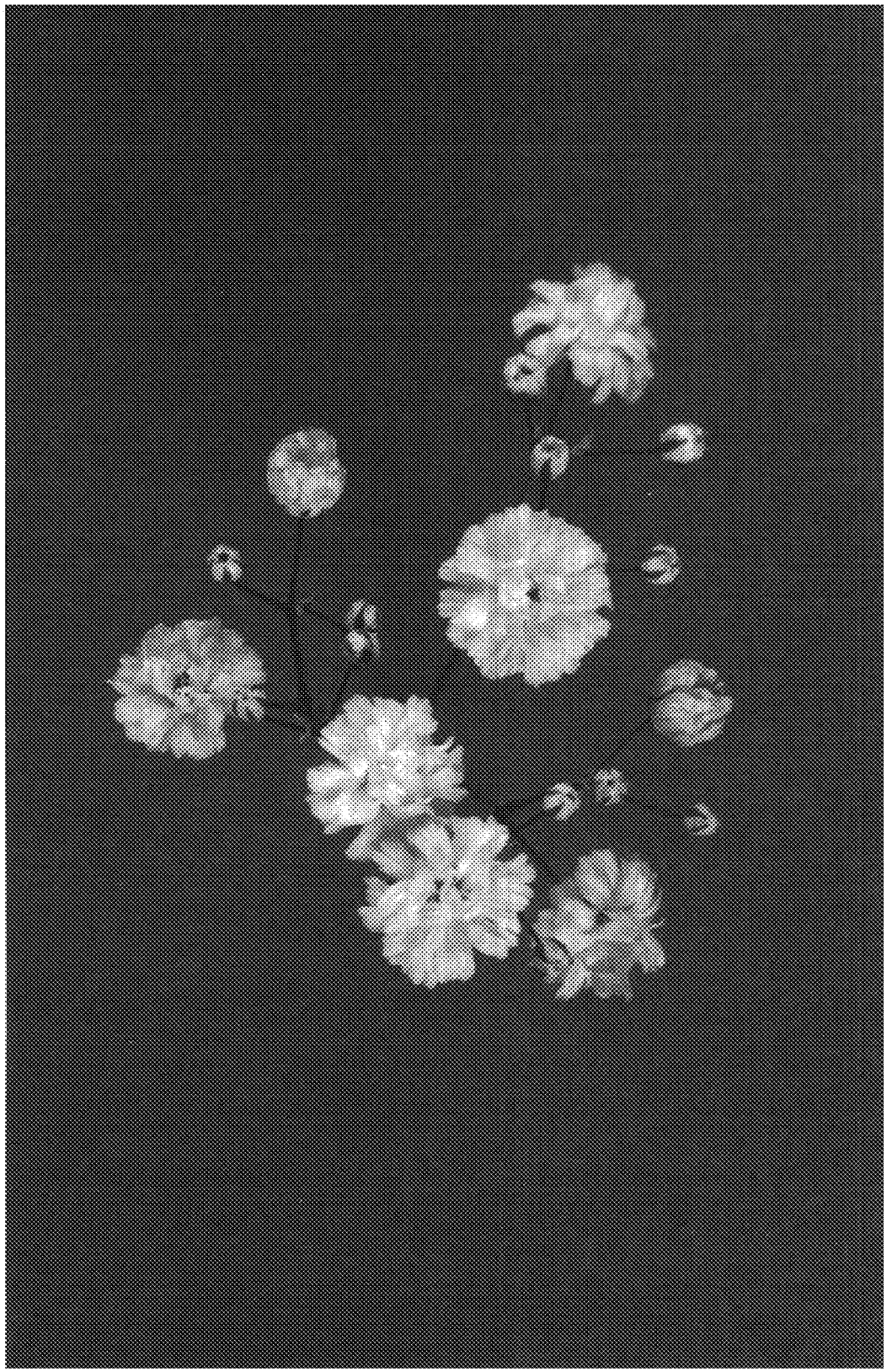

* * * * *